(12) United States Patent
Vincent et al.

(10) Patent No.: US 10,977,796 B2
(45) Date of Patent: Apr. 13, 2021

(54) PLATFORM FOR EVALUATING MEDICAL INFORMATION AND METHOD FOR USING THE SAME

(71) Applicant: FUJIFILM MEDICAL SYSTEMS U.S.A., INC., Stamford, CT (US)

(72) Inventors: Brigil Vincent, Morrisville, NC (US); Keiji Sugihara, Cary, NC (US); William B. Carruthers, III, Cary, NC (US); Yoshiyuki Kurami, Morrisville, NC (US)

(73) Assignee: Fujifilm Medical Systems U.S.A., Inc., Stamford, CT (US)

( * ) Notice: Subject to any disclaimer, the term of this patent is extended or adjusted under 35 U.S.C. 154(b) by 0 days.

(21) Appl. No.: 16/370,339

(22) Filed: Mar. 29, 2019

(65) Prior Publication Data
US 2020/0311938 A1 Oct. 1, 2020

(51) Int. Cl.
*G06T 7/00* (2017.01)
*G16H 70/00* (2018.01)
(Continued)

(52) U.S. Cl.
CPC .......... *G06T 7/0016* (2013.01); *G16H 10/20* (2018.01); *G16H 30/20* (2018.01); *G16H 70/00* (2018.01)

(58) Field of Classification Search
CPC .............................. G06T 7/0016; G16H 70/00
See application file for complete search history.

(56) References Cited

U.S. PATENT DOCUMENTS 8,813,024 B2 8/2014 Akkiraju et al.
8,949,403 B1 2/2015 Budzisch et al.
(Continued)

FOREIGN PATENT DOCUMENTS

JP 2009125226 6/2009
JP 2013128725 7/2013
WO 2016090326 6/2016

OTHER PUBLICATIONS

International Search Report for Application No. PCT/US2020/020516 dated Jul. 2, 2020, 10 pages.
(Continued)

*Primary Examiner* — Tuan H Nguyen
(74) *Attorney, Agent, or Firm* — Heslin Rothenberg Farley & Mesiti P.C.

(57) ABSTRACT

A platform for evaluating medical information and method for using the same are described. In one embodiment, the method comprises: monitoring, by a medical image management system, for a first indication of a content change at one or more data sources; determining, in response to the first indication, which of a plurality of image analysis engines is to analyze at least one image of one or more new medical images associated with the content change based on one or both of information accompanying the one or more images or results of applying body part detection on the at least one image; sending a first notification to start image analysis on the at least one image of the one or more medical images, the first notification being sent to each image analysis engine in a set of one or more image analysis engines determined to analyze the at least one image of the one or more new medical images; receiving a second indication that image analysis results are available from the set of one or more image analysis engines; and sending a
(Continued)

second notification to subscribers to indicate availability of image analysis results for access and display thereby.

24 Claims, 8 Drawing Sheets

(51) Int. Cl.
*G16H 10/20* (2018.01)
*G16H 30/20* (2018.01)

(56) References Cited

U.S. PATENT DOCUMENTS

| | | | |
|---|---|---|---|
| 9,704,094 B2 | 7/2017 | Amir et al. | |
| 2007/0238960 A1 | 10/2007 | Thorn | |
| 2015/0331995 A1* | 11/2015 | Zhao | G16H 40/63 705/2 |
| 2017/0255452 A1 | 9/2017 | Barnes et al. | |
| 2020/0211692 A1* | 7/2020 | Kalafut | G16H 30/40 |

OTHER PUBLICATIONS

Varun Goyal, System and Method for Integrating and Processing of Information from Plurality of Sources, India, Jun. 30, 2015, 42 pages.

\* cited by examiner

PLATFORM FOR EVALUATING MEDICAL INFORMATION AND METHOD FOR USING THE SAME

FIELD OF THE INVENTION

Embodiments of the present invention relate to the field of medical imaging; more particularly, embodiments of the present invention relate to using an automated image analysis (e.g., artificial intelligence (AI) analysis) platform to analyze medical images.

BACKGROUND

Physicians and other medical personnel often review all of a patient's relevant clinical information when making healthcare decisions. The clinical information is typically included in healthcare studies and structured reports. These often include information about a patient's history, diagnostic reports from different domains, images, and other clinical data in electronic format.

The healthcare studies of a patient include a diagnostic imaging report that contains parameter values (e.g., measurements, readings, etc.) and images from examinations or procedures that are usually shared among physicians and clinicians to help in diagnosis and treatment.

The healthcare studies are typically generated in response to a physician ordering an examination for their patient. The examination is performed and the generated study is often sent to a Picture Archiving and Communication System (PACS). A physician or clinician can use a medical image management system to obtain a worklist containing studies for their patients.

Various Artificial Intelligence (AI) algorithms have recently been utilized with Radiology PACS systems. These algorithms automate the process of evaluating images in the healthcare studies. These algorithms can be applied to single images or complete studies, and the results will be made accessible to the interpreting physician, as well as other clinical users. Even though algorithm results are available, the interpreting physician may be unaware of the findings because the AI algorithms are deployed in different platforms and there is no organized storage, access and data flow for the AI results. Because of these limitations, the interpreting physician may not be able to review the automated results in a timely manner, which could cause a patient more harm or delay in treatment if not reviewed with the quickness associated with the priority level of the findings.

SUMMARY OF THE INVENTION

A platform for evaluating medical information and method for using the same are described. In one embodiment, the method comprises: monitoring, by a medical image management system, for a first indication of a content change at one or more data sources; determining, in response to the first indication, which of a plurality of image analysis engines is to analyze at least one image of the one or more new medical images associated with the content change based on one or both of information accompanying the one or more images or results of applying body part detection on the at least one image; sending a first notification to start image analysis on the at least one image of the one or more medical images, the first notification being sent to each image analysis engine in a set of one or more image analysis engines determined to analyze the at least one image of the one or more new medical images; receiving a second indication that image analysis results are available from the set of one or more image analysis engines; and sending a second notification to subscribers to indicate availability of image analysis results for access and display thereby.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Embodiments of the present invention are directed to systems and methods, for performing an image analysis workflow with a platform for analyzing medical images. In one embodiment, the image analysis comprises artificial intelligence (AI) analysis that is used to analyze medical images as part of a workflow (e.g., a workflow in Radiology, a workflow in Cardiology, etc.). In one embodiment, the medical images are part of healthcare studies and the platform is an AI platform that is part of, or associated with, a medical image management system. In one embodiment, the AI Platform is an Open API-based platform in which multiple AI algorithms are integrated to establish seamless integration for AI workflow in different branches of medicine. By having multiple AI algorithms available to analyze medical images, there is a higher likelihood of identifying medical conditions in patients more quickly than in the prior art. This enables healthcare studies to present critical/emergent results at the top of the list, allowing for potentially quicker diagnosis. Having briefly described an overview of the present invention, embodiments of the invention will be discussed with reference to FIGS. 1-7.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
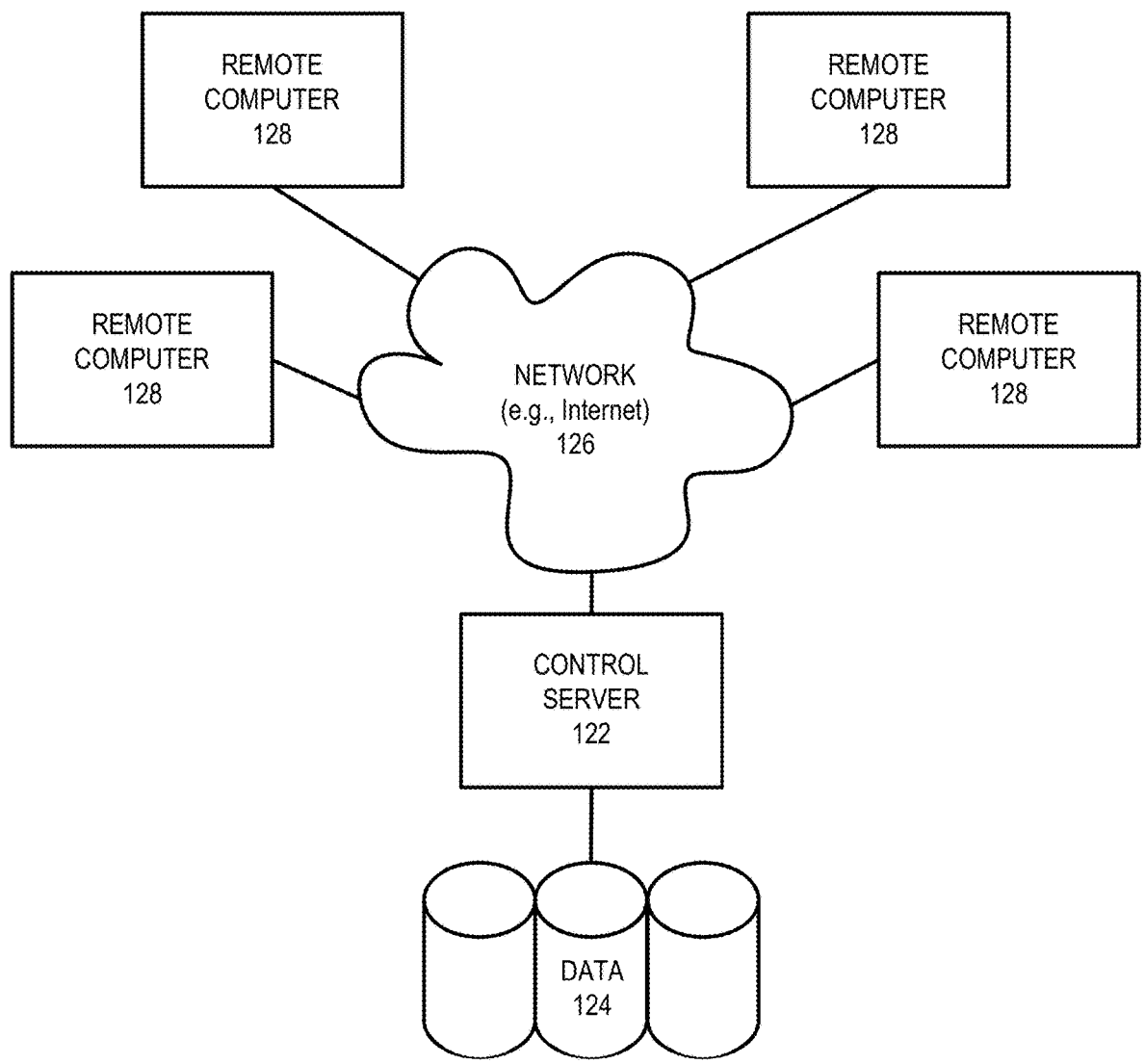
FIG. 1 illustrates an exemplary medical information computing system environment, with which embodiments of the present invention may be implemented.

Referring to the drawings in general, and initially to FIG. 1 in particular, a medical information computing system environment, with which embodiments of the present invention may be implemented is illustrated and designated generally as reference numeral 120. It will be understood and appreciated by those of ordinary skill in the art that the illustrated medical information computing system environment 120 is merely an example of one suitable computing environment and is not intended to suggest any limitation as to the scope of use or functionality of the invention. Neither should the medical information computing system environment 120 be interpreted as having any dependency or requirement relating to any single component or combination of components illustrated therein.

Embodiments of the present invention may be operational with numerous general-purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 120 includes a general-purpose computing device in the form of a control server 122. Components of control server 122 may include, without limitation, a processing unit, internal system memory, and a suitable system bus for coupling various system components, including database cluster 124, with control server 122. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Control server 122 typically includes therein, or has access to, a variety of computer-readable media, for instance, database cluster 124. Computer-readable media can be any available media that may be accessed by control server 122, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by control server 122. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 124, provide storage of computer-readable instructions, data structures, program modules, and other data for control server 122. Control server 122 may operate in a computer network 126 using logical connections to one or more remote computers 128. Remote computers 128 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, radiologic technologists, researchers, veterinarians, students, and the like. Remote computers 128 may also be physically located in non-traditional medical care environments so that the entire health care community may be capable of integration on the network. Remote computers 128 may be personal computers, servers, routers, network PCs, peer devices, other common network nodes, or the like, and may include some or all of the elements described above in relation to control server 122. The devices can be personal digital assistants or other like devices.

Exemplary computer networks 126 may include, without limitation, local area networks (LANs) and/or wide area networks (WANs). Such networking environments are commonplace in offices, enterprise-wide computer networks, intranets, and the Internet. When utilized in a WAN networking environment, the control server 122 may include a modem or other means for establishing communications over the WAN, such as the Internet. In a networked environment, program modules or portions thereof may be stored in association with control server 122, the database cluster 124, or any of remote computers 128. For example, and not by way of limitation, various application programs may reside on the memory associated with any one or more of remote computers 128. It will be appreciated by those of ordinary skill in the art that the network connections shown are exemplary and other means of establishing a communications link between the computers (e.g., control server 122 and remote computers 128) may be utilized.

In operation, a clinician may enter commands and information into control server 122 or convey the commands and information to control server 122 via one or more of remote computers 128 through input devices, such as a keyboard, a pointing device (commonly referred to as a mouse), a trackball, or a touch pad. Other input devices may include, without limitation, microphones, scanners, or the like. Commands and information may also be sent directly from a remote healthcare device to the control server 122. In addition to a monitor, control server 122 and/or remote computers 128 may include other peripheral output devices, such as speakers and a printer.

Although many other internal components of control server 122 and remote computers 128 are not shown, those of ordinary skill in the art will appreciate that such components and their interconnection are well known. Accordingly, additional details concerning the internal construction of control server 122 and remote computers 128 are not further disclosed herein.

Figure 2:
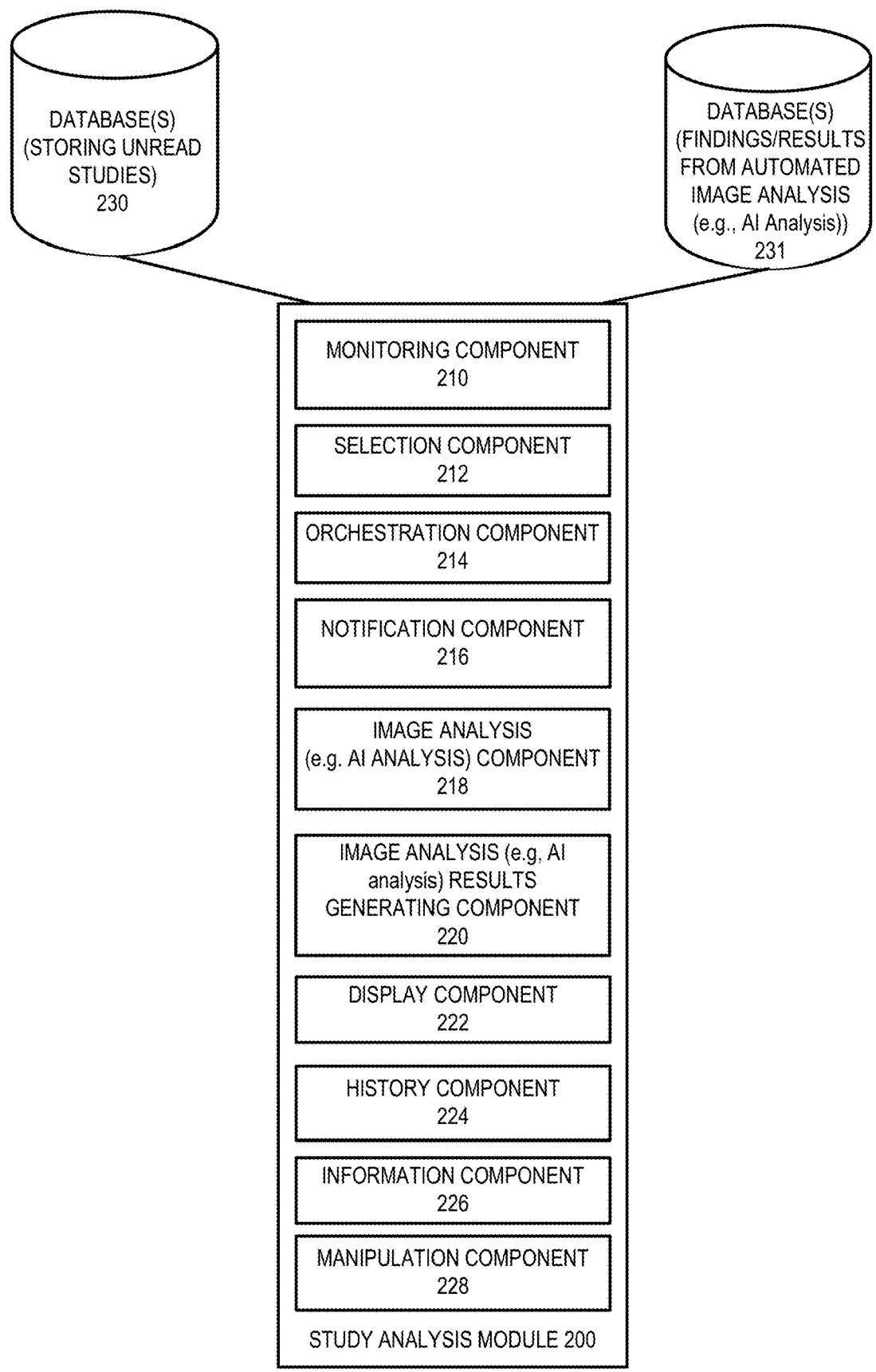
FIG. 2 is a block diagram showing one embodiment of a computing system architecture for analyzing study healthcare study information (e.g., images,).

With reference to FIG. 2, a block diagram is illustrated that shows an example of a computing system architecture for performing image analysis (e.g., artificial intelligence (AI) analysis on medical images). It will be appreciated that the computing system architecture shown in FIG. 2 is merely an example of one suitable computing system and is not intended as having any dependency or requirement related to any single module/component or combination of modules/components.

In one embodiment, the computing system includes a study analysis 200, one or more databases 230 storing and maintaining unread healthcare studies or existing healthcare studies that contain new medical images (and potentially other healthcare studies), and one or more databases 231 storing and maintaining findings that result from applying one or more automated image analysis algorithms (e.g., artificial intelligence (AI) analysis algorithms) to images of the unread healthcare studies such as those, for example, stored in databases 230. In one embodiment, databases 230 and 231 are the same set of databases.

In one embodiment, the healthcare studies include images and study data, such as, for example, values of one or more medical parameters (e.g., measurements, etc.) related to the healthcare study. Exemplary medical images include radiology images, laboratory images, pictures, cardiology images, such as echocardiography images, and other healthcare images. One of skill in the art will appreciate that the databases may be maintained separately or may be integrated. Databases 230 may contain images or other study data (e.g., parameter values (e.g., measurements)) that are linked to a patient's electronic medical record (EMR), such that images and/or study data may be selected from within the EMR and displayed within a viewer via display component 222 or linked to a VNA (Vendor Neutral Archive) which stores, images, EKG's pictures, notes, etc. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way.

In one embodiment, the automated image analysis algorithms are AI analysis algorithms performed on the one or more images of healthcare studies. These algorithms may be applied remotely using one or more servers (e.g., AI engines and applications) that are in communication with a medical image management platform. These servers receive the studies and their associated images and automatically apply the algorithms to those images. Alternatively, the AI analysis algorithms are integrated into the platform and applied locally on the images of the healthcare studies by image analysis component 218 after the studies have been received by the medical image management system. Alternatively, some of the algorithms are performed remotely while others are performed locally.

The AI algorithms (or other image analysis algorithms) produce findings that specify the results of the application of the algorithms on the images. In one embodiment, these AI algorithms produce textual findings that indicate possible conditions of a patient identified by the algorithm. In one embodiment, the findings include a score (e.g., abnormality score, numerical confidence level indication associated with analysis results, etc.) prepared by the automated image analysis algorithm. For example, an abnormality score with a magnitude that indicates a chance the patient has an abnormality based on the analysis performed on the images (e.g., the higher the score, the higher the chance). Note that in alternative embodiments, other scores, such as confidence levels of diagnosis, may be included in the findings from the algorithms.

Study analysis module 200 includes a monitoring component 210 that monitors data sources for changes in content such as the storage of new healthcare studies or healthcare studies that have new medical images. These data sources may be PACS, VNA or other repository or database systems. These healthcare studies may come from more than one source (e.g., database). Study analysis module 200 may reside on one or more computing devices, such as, for example, control server 122 described above with reference to FIG. 1. By way of example, in one embodiment, control server 122 includes a computer processor and may be a server, personal computer, desktop computer, laptop computer, handheld device, mobile device, consumer electronic device, or the like.

In one embodiment, study analysis module 200 comprises selection component 212, orchestration component 214, a notification component 216, an image analysis (e.g., AI analysis) component 218, and an image analysis (e.g., AI analysis) results generation component 220. In various embodiments, study analysis module 200 includes a display component 222, a history component 224, an information component 226, and a manipulation component 228. It will be appreciated that while receiving healthcare studies stored in databases 230, study analysis module 200 may receive healthcare studies from multiple sources including databases spread across multiple facilities and/or multiple locations as well as findings that result from applying one or more automated image analysis algorithms (e.g., AI analysis algorithms) to images of the healthcare studies. It will also be appreciated that study analysis module 200 may receive healthcare studies with their images and/or findings that result from the automated image analysis algorithms (e.g., AI analysis algorithms) from the sources described above via links within a patient's EMR.

In response to monitoring component 210 determining that new content exists in one or more of the data sources, selection component 212 selects each healthcare study that is new or has new medical images and the data sources are accessed to obtain such studies. In one embodiment, the healthcare study comprises one or more series of images and one or more parameter values (e.g., measurements, findings, impressions, patient demographics and history/risk factors, etc.). In one embodiment, each series comprises one or more images depicting the subject of the image from various angles. A list perspective within a multimedia manager provides a list of available studies (including unread studies), images, and other media.

Orchestration component 214 determines which image analysis algorithms should be applied to analyze the new medical images. In one embodiment, orchestration component 214 determines which images of the new medical images are to be analyzed and which AI algorithms should perform the analysis. In one embodiment, the AI algorithms are performed by AI engines or AI applications of the image analysis (e.g., AI analysis) component 218. In one embodiment, an AI engine comprises circuitry that implements logic and/or executes software. The software may be an application. Based on the determination, orchestration component 214 assigns the AI algorithms of image analysis component 218 the images they are to evaluate.

Notification component 216 notifies the AI engines or systems (e.g., servers) running the AI algorithms regarding their assignments with respect to analyzing the new medical images. In one embodiment, notification component 216 sends a study identifier and information regarding which images to evaluate as part of the notifications, and in response thereto, image analysis component 218 obtains for evaluation the images from the data source in which they are stored. Alternatively, notification component 216 sends that actually images that are to be analyzed.

Once the images have been obtained, image analysis component 218 performs the AI or other image analysis on the images to produce findings. In one embodiment, this includes activating one or more AI algorithms executing on one or more AI engines or servers. One or more of the AI engines or servers maybe internal to the AI platform or external to the AI platform. In one embodiment, multiple AI engines or servers may be performing their analysis at the same time on the same or different medical images. Each of the AI algorithms produces results that are indicative of the findings of the algorithm. As part of the findings, the AI algorithms may include images, or portions thereof, that are relevant to diagnosis or condition of the patient associated with the image that was analyzed. Image analysis results generation component 220 takes the findings from AI algorithms of image analysis component 218 and generates outputs that are sent for review and stored for subsequent access.

Display component 222 includes a graphical display device that may be a monitor, computer screen, project device or other hardware device for displaying graphical user interfaces containing images and other data from healthcare studies as well as findings that result from applying automated image analysis algorithms to images in the healthcare studies. In one embodiment, display component 222 displays the GUI with the list of unread healthcare studies or healthcare studies with new images along with priority information highlighting those studies with findings that are more urgent or critical. In one embodiment, the list of unread healthcare studies is sorted based on priority. In another embodiment, the list of healthcare studies is not sorted but the priority information clearly shown so that a physician is able to discern priority levels from the state of the display of unread healthcare studies (e.g., have higher priority and/or lower priority).

In one embodiment, a history component 224 displays a history of different studies and clinical images associated with more than one healthcare image. History component 224 further allows a selection of one or more images from the history to be displayed in the viewer by display component 222. For example, the selection component 212 may have received a selection from the clinician of a particular study. However, once display component 222 has displayed the images that comprise that selected study, history component 224 may display other studies and clinical images that are of particular interest to the clinician. The clinician may then select additional items from the history to launch within the viewer.

In one embodiment, information component 226 displays additional information associated with more than one healthcare image, the history, or a combination thereof. The additional information comprises patient identifying information, image related information, study related information, or a combination thereof. Such additional information may also include time related information.

In one embodiment, a manipulation component 228 allows a clinician to manipulate a display of a healthcare image. For example, a clinician may determine that the image as it is rendered within the viewer is not large enough to see a desired level of detail. The clinician may zoom in or out and manipulation component 228 manipulates the display of the image accordingly. Similarly, the clinician may desire to pan an image and the manipulation component 228 manipulates the image display accordingly.

Figure 3:
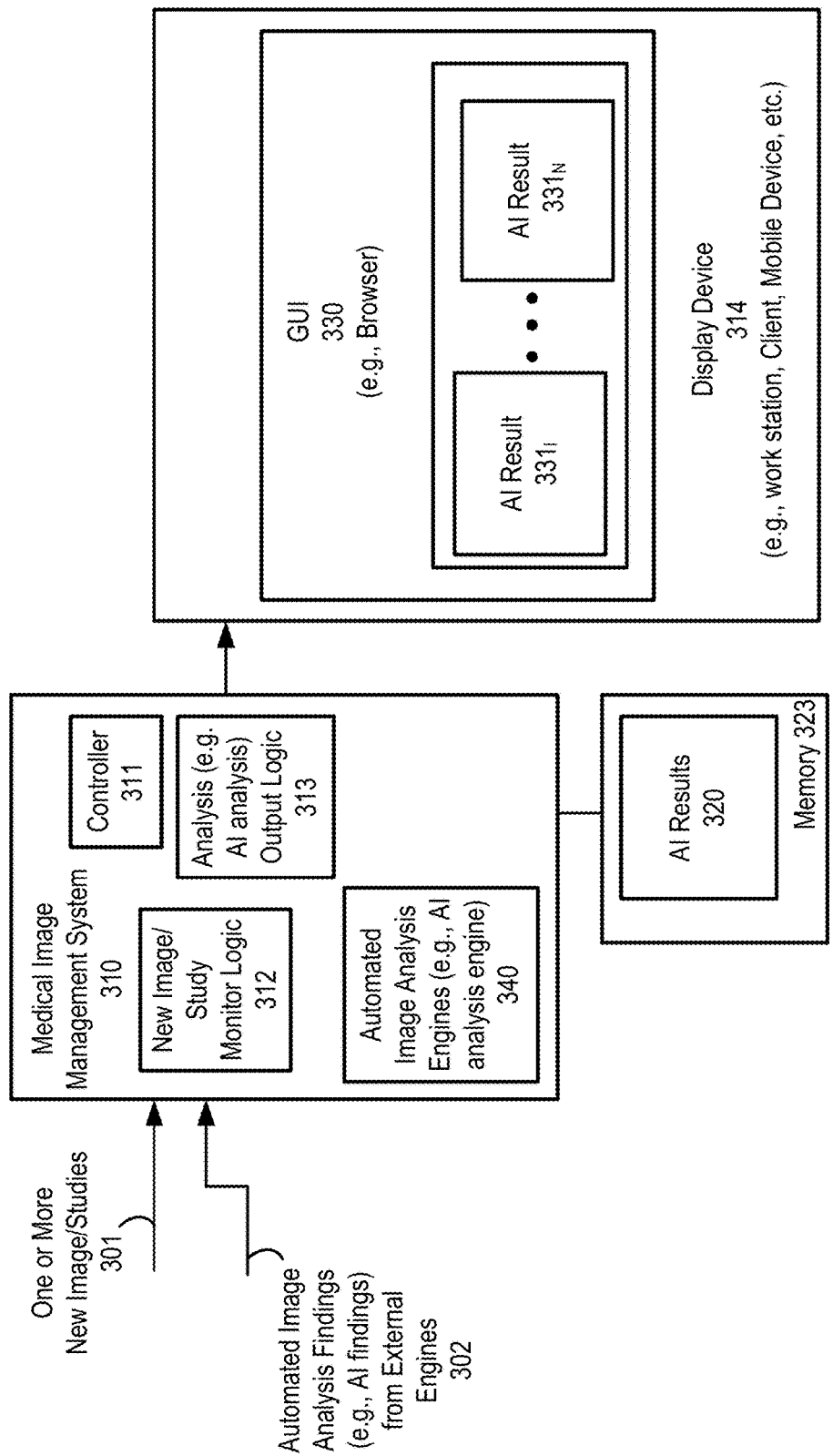
FIG. 3 is a data flow diagram of one embodiment of a process for analyzing medical images using automated image analysis algorithms (e.g., AI algorithms) that have been applied to one or more of the medical images.

FIG. 3 is a data flow diagram of one embodiment of a process for automatically analyzing images of healthcare studies using automated image analysis algorithms (e.g., AI analysis algorithm, etc.) that have been applied to one or more of the images of the healthcare studies.

Referring to FIG. 3, medical image management system 310 receives one or more healthcare studies 301. Healthcare studies 301 may include unread healthcare studies or healthcare studies with one or more new images. In one embodiment, medical image management system 310 receives healthcare studies 301 in response to monitoring logic 312 that monitors data sources for nee healthcare studies and/or healthcare studies with new images for evaluation. In one embodiment, one or more unread healthcare studies 301 are sent from one or more medical imaging modalities that perform medical imaging (e.g., cardiovascular (CV), X-ray radiography, magnetic resonance imaging, ultrasound, endoscopy, tactile imaging, thermography, nuclear medicine functional imaging techniques such as positron emission tomography (PET) and single-photon emission computed tomography (SPECT), etc.). In another embodiment, one or more healthcare studies 301 are received by medical image management system 310 from a remote location. In one embodiment, the remote location may comprise one or more modalities that create the studies or a remotely located image repository (e.g., a picture archiving and communication system (PACS), VNA, etc.).

In one embodiment, monitoring logic 312 monitors for a first indication of a content change at one or more data sources (e.g., arrival of the new medical images that are part of a new health care study or an existing study created prior to generation of the new medical images) and obtains those studies in response to determining a content change has occurred. In one embodiment, monitoring logic 312 determines a content change has occurred in response to receiving notifications from the data sources storing the healthcare studies or modalities/facilities generating the healthcare studies indicating that such studies are available for review and evaluation. In response to these notifications, monitoring logic 312 access the data sources storing the studies to obtain them. The access may include a request to the data source for a copy of the study. The request may be sent directly or over a network connection to the data source. In one embodiment, medical image management system 310 comprises a network communication interface(s) (not shown) to send the request to the data source for a copy of the study receive healthcare studies and receive studies. In another embodiment, medical image management system 310 requests and receives studies over a direct connection with individual data sources.

In one embodiment, medical image management system 310 comprises a memory, such as, for example, memory 323, to store received healthcare studies that it has received.

In on embodiment, after obtaining the healthcare studies with medical images to be analyzed, controller 311 (e.g., one or more processors) determines which of a plurality of image analysis engines 340 (e.g., one or more artificial intelligence (AI) engines) is to analyze at least one of the new medical images. This is referred to herein as image analysis (e.g., AI analysis) orchestration. To those image analysis engines of image analysis engines 340 identified to evaluate the medical images, controller 311 sends a notification to cause those image analysis engines to initiate image analysis on one or more of the new medical images. In one embodiment, the determination of which image analysis engines is based on information accompanying the one or more images and/or results of applying body part detection on at least one of the new images.

In one embodiment, each of the automated analysis engines (e.g., AI image analysis engines) performs analysis on images and/or non-image data of the healthcare studies. Examples of non-image data include, but are not limited to, text, waveforms, time-series, structured/template-based reports. In one embodiment, these engines may be integrated into the medical image management system, such as shown with automated image analysis engines (e.g., AI analysis engines, etc.) 340. In another embodiment, one or more of these engines 302 are located remotely with respect to the medical image management system. In one embodiment, image analysis engines 340 produces findings, or results 320. In one embodiment, individual analysis engines produce finding based on image analysis alone while other analysis engines produce findings based on a combination of image and data analysis. In one embodiment, the findings from applying automated image analysis algorithms of image analysis engines 340 include an abnormality score where the higher the number of the abnormality score, the greater chance of an abnormality was identified on one or more images in a study by the AI or other image analysis. In one embodiment, the findings from applying automated image analysis algorithms of image analysis engines 340 may include an indication that nothing has been found in the image(s) and/or non-image data. The results (findings) from applying these engines to the images are sent, via wired or wireless communications, to the medical image management system 310.

After analyzing the images and/or non-images and producing the findings, the image analysis engines 340 send indications that their results have been generated and send the results themselves to the platform. In response, the platform sends notifications to subscribers to indicate availability of image analysis results for access and display.

After the healthcare studies 301 and the automated image analysis (e.g., AI analysis has been performed by image analysis engines 340 to obtain findings, output logic 313 obtains AI and other image analysis results 320 from memory 323 and uses that information to display AI result $331_1$-$331_N$ in a GUI (or viewer) 330 on display device 314. In one embodiment, the AI results are displayed along with all or a portion of the study containing the image that was evaluated by one of AI engines 340 to create the AI result. That is, display 314 allows a user to display, within a graphical user interface 330, one or more healthcare studies, or portions thereof, along with AI or other image analysis results, such as, for example, AI results $331_1$-$331_N$. This allows a physician or other medical profession to easily see the studies that have been received and the results of the image analysis that has been performed.

In one embodiment, controller 311 also controls other operations of medical image management system 310. In one embodiment, controller 311 comprises one or more processors, microcontrollers, and/or a combination of hardware, software and/or firmware.

Figure 4A:
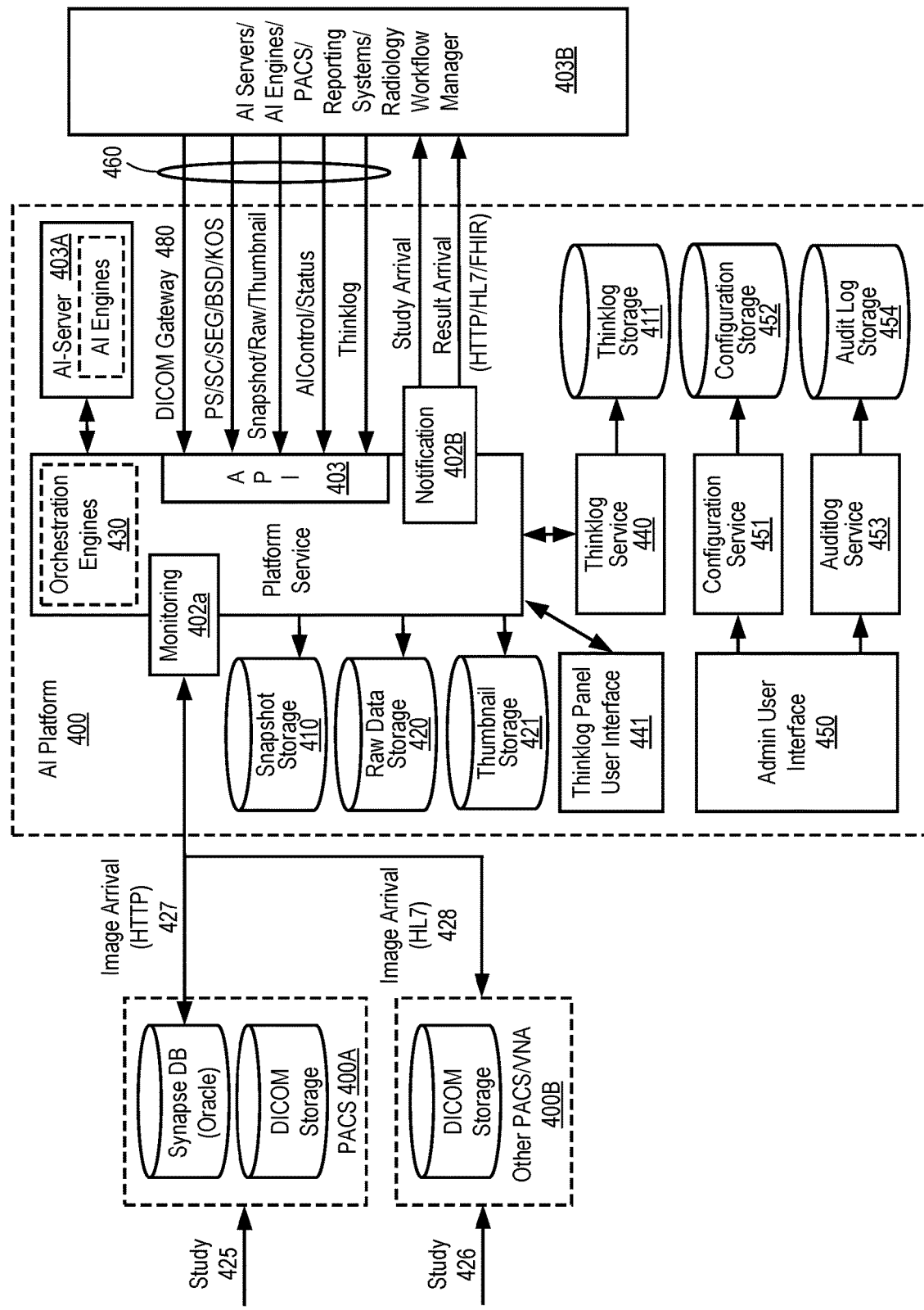
FIG. 4A is a block diagram of one embodiment of an AI platform for use in performing image analysis on medical images.
Figure 4B:
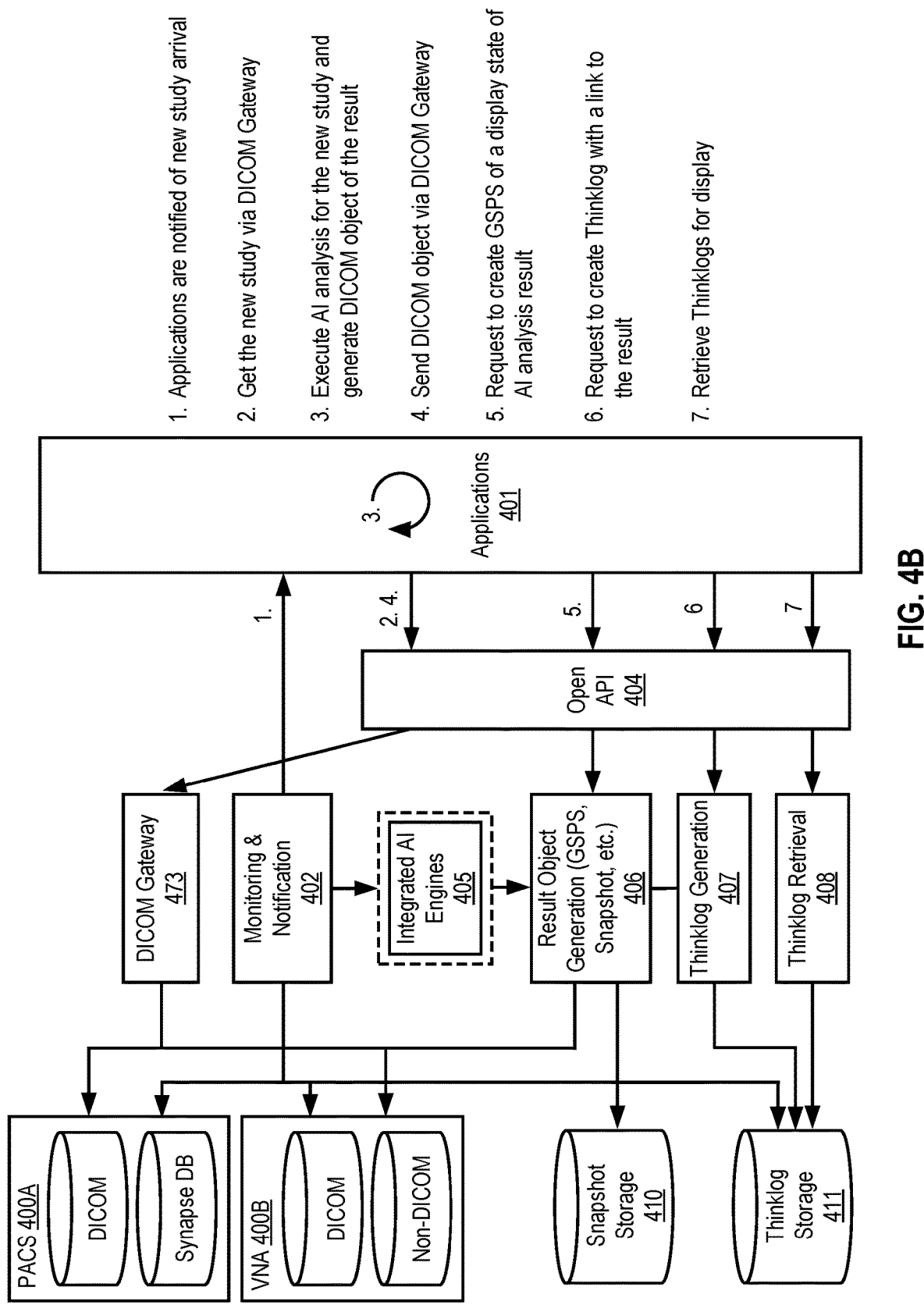
FIG. 4B is a data flow diagram of one embodiment of an AI platform for use in performing image analysis on medical images.

FIGS. 4A and 4B illustrate one embodiment of an architecture for an AI platform that is part of a medical image management system, such as medical image management system 310 of FIG. 3. In one embodiment, the AI platform architecture of FIGS. 4A and 4B includes a number of components to perform the operations described herein, including the following features: Open APIs 403, monitoring logic 402a, orchestration engines 430 to perform image analysis (e.g., AI analysis) orchestration, integration of AI engines 403A into the platform, study notification logic 402B, image analysis (e.g., AI) scanning, use of one or more AI servers (e.g., server 403B), one or more built-in AI server (e.g., server 403A), and image analysis result (e.g., AI result) notification logic 460. Each of these will be described in more detail below. In one embodiment, AI scanning refers to one or more AI engines or algorithms processing images and producing result data. In another embodiment, scanning a study also means the whole process of dividing a study into pieces and sending it to individual AI algorithms (orchestrating) plus the individual AI processing.

The AI platform provides Open APIs 403 to applications (e.g., applications 401, applications running on AI servers 403A, 403B, etc.) and AI engines (e.g., 403A, 403B) in order to effectively perform AI evaluation within a medical workflow (e.g., a radiology workflow). In one embodiment, open APIs 403 enable use of a DICOM (Digital Imaging and Communications in Medicine) gateway (e.g., 480, 473) to access DICOM information. In one embodiment, the DICOM gateway (e.g., 480, 473) is used to access DICOM information via QIDO-RS, WADO-RS and STOW-RS.

In one embodiment, Open APIs 403 offers a mechanism and data models to work with DICOM GSPS, DICOM Segmentation, Secondary Capture, Basic Structured Display, Key Object Selection, Structured Reports, etc., without having to implement DICOM conformance by applications (e.g., 401) or AI engines (e.g., 403A, 403B). As is described in more detail below, in one embodiment, open APIs 403 include APIs to query, retrieve and create thinklog instances which help to manage and access image analysis (e.g., AI analysis) results in an organized way across multiple systems. For more information on thinklogs, see patent application Ser. No. 14/820,144, titled "METHODS AND APPA- RATUS FOR LOGGING INFORMATION USING A MEDICAL IMAGING DISPLAY SYSTEM," filed on Aug. 6, 2015.

In one embodiment, open API 403 also offers access to AI engines (e.g., 403A, 403B) and scanning workflow in such a way that applications (e.g., 401) can trigger an AI scan and track status of an AI scan, or AI analysis.

In one embodiment, the AI Platform is integrated with a PACS system (400A, 400B) and/or a VNA. In one embodiment, AI Platform configures the PACS systems and VNAs as data sources. Thus, when the PACS systems (400A, 400B) and the VNA receive studies (e.g., 425, 426), over for example a wired or wireless network connection, the AI platform is able to obtain them.

Once connected to PACS systems 400A and 400B, the AI Platform uses monitoring logic 402A to continuously monitor the content changes in the data source including new study arrival, arrival of DICOM images or non-DICOM images to an existing study, or other arrivals of new images. In one embodiment, monitoring logic 402A achieves study monitoring through a custom integration and through standard interfaces (e.g., HL7/FHIR). In one embodiment, the custom integration involves monitoring logic 402A being notified that new images have arrived via a notification (e.g., image arrival 427) identifies the study with the new images via, for example, a study identifier (ID), and identifies an indication of what change occurred (e.g., a new study arrived, new images added to a study along with identification information (e.g., metadata) to specify the new images among all the images in the study and the type of information (e.g., body part(s)) are depicted in the new images. In one embodiment, the image arrival notification is via a HTTP communication (e.g., POST). In contrast, monitoring logic 402A also uses standard interfaces to receive an indication that there is a content change (e.g., a new study or new images provided as image arrival 428) in a data source, such as PACS systems 400A and 400B. In one embodiment, this indication does not include information identifying the change that had occurred. In such cases, the study is accessed and analyzed to determine the new content and which of the image analysis engines is appropriate to review the new content.

Upon identifying content change in PACS/VNA, AI platform 400 acquires the study and performs AI orchestration using orchestration engines 430 to decide which of the AI algorithms needs to be assigned to evaluate the study. In one embodiment, orchestration engines 430 perform orchestration by utilizing various header-based filters (e.g., DICOM header-based filters) to obtain and evaluate information stored in the headers of the image files. For example, the header information in an image, series of images, or study may specify the contents (e.g., body part, type of examination, etc.) that could be used to identify appropriate image analysis engines to evaluate the study. In one embodiment, orchestration engines 430 use built-in body part detection algorithms to determine the body part(s) depicted in the images to identify the AI engines (403A, 403B) appropriate to analyze images with those types of body parts.

Orchestration engines 430 may identify multiple AI engines that are to evaluate a study. In one embodiment, when multiple AI engines require evaluating a study, orchestration engines 430 of AI platform 400 decides the priority for each AI engine (or each AI algorithm that is to be performed) and assigns the task of evaluating the study based on the priority. In one embodiment, orchestration engines 430 determine the priority based on features in the study, its prior studies (e.g., a study acquired for the same patient prior to the current study) and/or nature of algorithms. For example, with respect to prior studies, when the AI platform (e.g., AI platform 400) scans a study with AI algorithms, some of the AI scans require its prior study because it will perform an AI analysis (i.e., an AI scan) on the prior study as well. With respect to priority, for example, if the AI algorithm is for detecting cerebral hemorrhage, it should be executed with a high priority since such a hemorrhage should be immediately treated if it exists. Assigning priorities is also used when multiple images from different studies are available for evaluation at the same time by one AI engine that only handles one image analysis at a time.

Based on the orchestration decisions taken by orchestration engines 430, AI platform 400 notifies AI servers (403A, 403B) or applications (401) that have been integrated into AI platform 400. These AI engines can be hosted inside AI platform 400 (e.g., AI engines 403A) or can be hosted in separate AI server (e.g., AI server 403B) that is external to the platform. In different embodiments, AI server 403B can live either on premise environment or in a cloud environment. AI platform 400 provides Open APIs 403 that are utilized by applications or AI engines (401, 403A, 403B) to access data (e.g., studies, images) or stores findings (e.g., AI results).

In one embodiment, the notification is sent by notification logic 402B and includes information about the study and images to be analyzed. In one embodiment, AI applications or AI engines (401, 403A, 403B) are able to receive notifications from AI platform 400, via notification logic 402B, to start AI evaluation on the study. In one embodiment, applications or AI engines (401, 403A, 403B) are subscribers, in that they subscribe to receive the notification if it meets particular characteristics. For example, in one embodiment, orchestration engines 430 use predefined filters and algorithm properties to determine if the images for review have particular characteristics that meet the requirements of an AI server to which it could be sent for evaluation.

Upon receiving notification, application or AI engine (401, 403A, 403B) retrieves the images to be reviewed (e.g., DICOM images) from AI platform 400 through DICOM Gateway APIs 480 and analyzes one or more new images. The results of the analysis include findings or AI results.

In one embodiment, AI platform has built-in AI server 403A on which multiple company-specific AI engines are integrated and deployed. In one embodiment, notifications to AI server 403A are queued and processed based on the priority assigned by orchestration engines 430 and other scalability considerations. In one embodiment, AI platform 400 acquires and caches DICOM instances from data source specified in the notification message, using DICOM gateway APIs 480. AI Platform 400 analyzes the data and prepares input required for the AI engines. The input preparation includes preparation of DICOM headers and pixel data required for the engine. In one embodiment, some engines require reformatted 3D volume for processing the images, and AI platform 400 performs reconstruction, prepares the volumes in suitable plane and feeds the AI engine with the processed data. In one embodiment, AI engines of AI server 403A utilize the input to evaluate the DICOM images to detect various findings (abnormalities and diseases) and organs.

Each AI engine or application generates various forms of results which represents corresponding findings and store them back using corresponding Open APIs. In one embodiment, the results include one or more of, but not limited to, DICOM Grayscale Softcopy Presentation State (GSPS), DICOM structure report (SR), a snapshot or DICOM Basic Structured Display, raw data (e.g., DICOM or Non-DICOM), a DICOM Key Object Selection Document (KOS), etc. For more information on snapshots, see U.S. patent application Ser. No. 14/736,550, titled "METHODS AND APPARATUS FOR OBTAINING A SNAPSHOT OF A MEDICAL IMAGING DISPLAY," filed on Jun. 11, 2015. In one embodiment, AI platform 400 stores AI results in one or more storage devices, such as, for example, snapshot storage 410, raw data storage 420, and thumbnail storage 421.

In one embodiment, an Open API provides simplified APIs and data models in order to generate DICOM complaint AI result representations without having to implement DICOM conformance. For example, a heat-map can be stored as DICOM Segmentation instance using a Segmentation Open API, without having to implement DICOM Segmentation by application or AI engine (401, 403A, 403B). In addition to the individual result instances, in one embodiment, applications or AI engine (401, 403A, 403B) create a thinklog instance using a summary of result where findings details, related AI result instances and key images representative of the findings and/or AI result instances will be referenced. The thinklog instance manages the AI findings in an organized way. In one embodiment, the thinklog instances are displayed using thinklog panel user interface 441 under control of thinklog service 440. In one embodiment, thinklogs are stored in thinklog storage 411.

Once the AI scan result is ready and a thinklog instance is generated, if any, AI platform 400 send notification about the AI results arrival to a certain predefined set of individuals or locations. In one embodiment, the notification regarding the arrival of the AI results is sent all subscribed applications. In one embodiment, AI platform 400 supports different notification mechanism including WebInvoke, SignalR, HL7 and FHIR in order to allow various types of systems or application to utilize the AI results. Systems consuming the AI result notification include, for example, but not limited to, Radiology Workflow Manager, Image Viewing workstation, Billing IT systems etc. In response to the notification, applications (401) can then utilize the AI analysis results by accessing thinklog and each of the results generated by AI engines (403A, 403B).

In one embodiment, AI platform 400 includes an administration user interface 450 through which a user can configure AI platform 400, or view configuration information thereof, under control of configuration service 451, with the use of information stored in configuration storage 452. In one embodiment, an administration user interface 450 allows a user to review an audit log for AI platform 400, or view audit information thereof, under control of audit log service 453, with the use of information stored in audit log storage 454.

Figure 5:
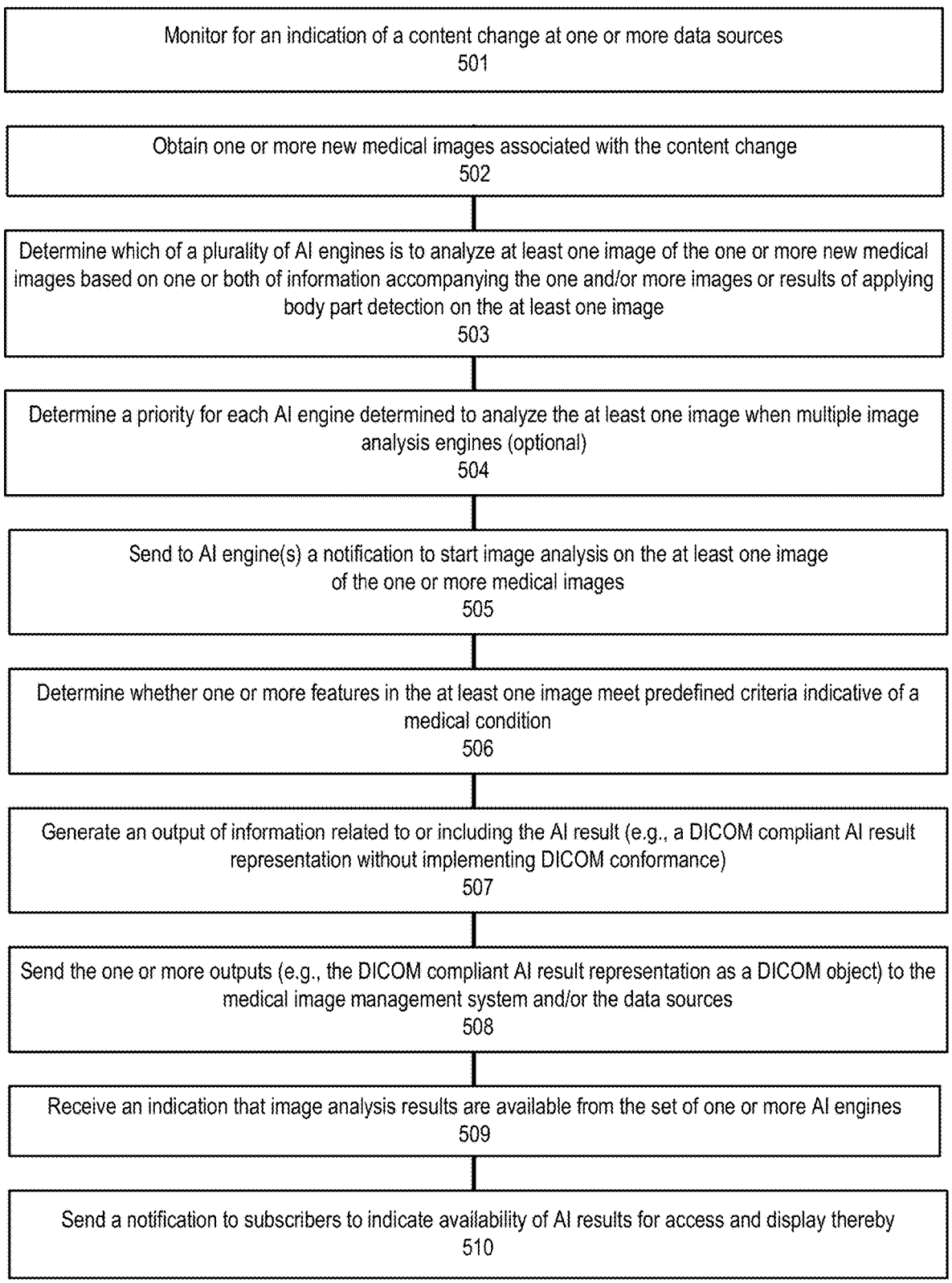
FIG. 5 is a flow diagram of one embodiment of a process for processing medical images using an image analysis (e.g., AI analysis) platform.

FIG. 5 is a flow diagram of one embodiment of a process for processing medical images. In one embodiment, the processes are performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 3, 4A and 4B.

Referring to FIG. 5, the process begins by processing logic monitoring for an indication of a content change at one or more data sources (processing block 501). In one embodiment, this indication specifies arrival of the one or more new medical images to the one or more data sources. In one embodiment, these new medical images are part of a new health care study or an existing study created prior to generation of the new medical images.

In response to the indication, in one embodiment, processing logic obtains one or more new medical images associated with the content change (processing block 502) and determines which of a plurality of AI/image analysis engines (e.g., applications) is to analyze at least one image of the new medical images based on one or both of information accompanying the one or more images and/or results of applying body part detection on the at least one image (processing block 503).

In another embodiment, processing logic of the medical management system does not necessarily obtain the new images for the AI engines. In one embodiment, this depends on the level of integration between the AI platform (e.g., AI platform 400) and the AI engines. For examples, some AI algorithms are tightly integrated in such a way that the system provides actual image pixel data or reconstructed 3D volume. This is an example of a PUSH model where algorithm/engine obtains data from AI platform (e.g., AI platform 400) and it doesn't have to fetch images from a PACS or VNA. In another embodiment, another integration level that is used is a PULL model where the AI engine has to pull data from PACS/VNA. In one embodiment, this is based on the UID information that the AI platform (e.g., AI platform 400) provides to the AI engine. To PULL data from VNA or PACS, the AI platform (e.g., AI platform 400) provides DICOM Gateway APIs that are used. In one embodiment, at least one of the AI/image analysis engines comprises an artificial intelligence (AI) engine.

If multiple image analysis engines (e.g., AI engines or applications) are to evaluate sets of new medical images, in one embodiment, processing logic determines a priority for each AI/image analysis engine that indicates when that AI/image analysis engine is to analyze the at least one image when multiple AI/image analysis engines (processing block 504). In one embodiment, processing logic determines the priority based on features in a healthcare study of the at least one image, priors and a nature of the multiple AI/image analysis engines.

After determining the image analysis engines that are to analyze the images, processing logic sends a notification to the AI engine/image analysis engine to start AI/image analysis on the at least one image of the new medical images (processing block 505). In one embodiment, this notification is sent to each AI engine/image analysis engine that has been assigned to analyze at least one image of the new medical images.

In response to receiving the notification, processing logic of the AI/image analysis engine determines whether one or more features in the at least one image meet predefined criteria indicative of a medical condition (processing block 506). In one embodiment, the one or more features include one or more of anatomical features and abnormalities set forth in the medical image. In one embodiment, the AI/image analysis engine is operable to perform AI/image analysis to determine whether the one or more features in the at least one image meet the predefined criteria without user input.

After performing the AI/image analysis, processing logic of the AI/image analysis engine generates an output of information related to or including the AI result (e.g., a DICOM compliant AI result representation without implementing DICOM conformance) (processing block 507) and sends the one or more outputs (e.g., the DICOM compliant AI result representation as a DICOM object) to the medical image management system and/or the data sources (e.g., PACS, VNA, etc.) for storage therein (processing block 508). In one embodiment, the one or more outputs generated by some AI engines are a non-DICOM AI result or non-DICOM-compliant results. In one embodiment, this occurs when there are no findings. Processing logic also receives an indication that AI/image analysis results are available from the set of AI/image analysis engines (processing block 509) and sends a notification to subscribers to indicate availability of AI/image analysis results for access and display thereby (processing block 510).

Figure 6:
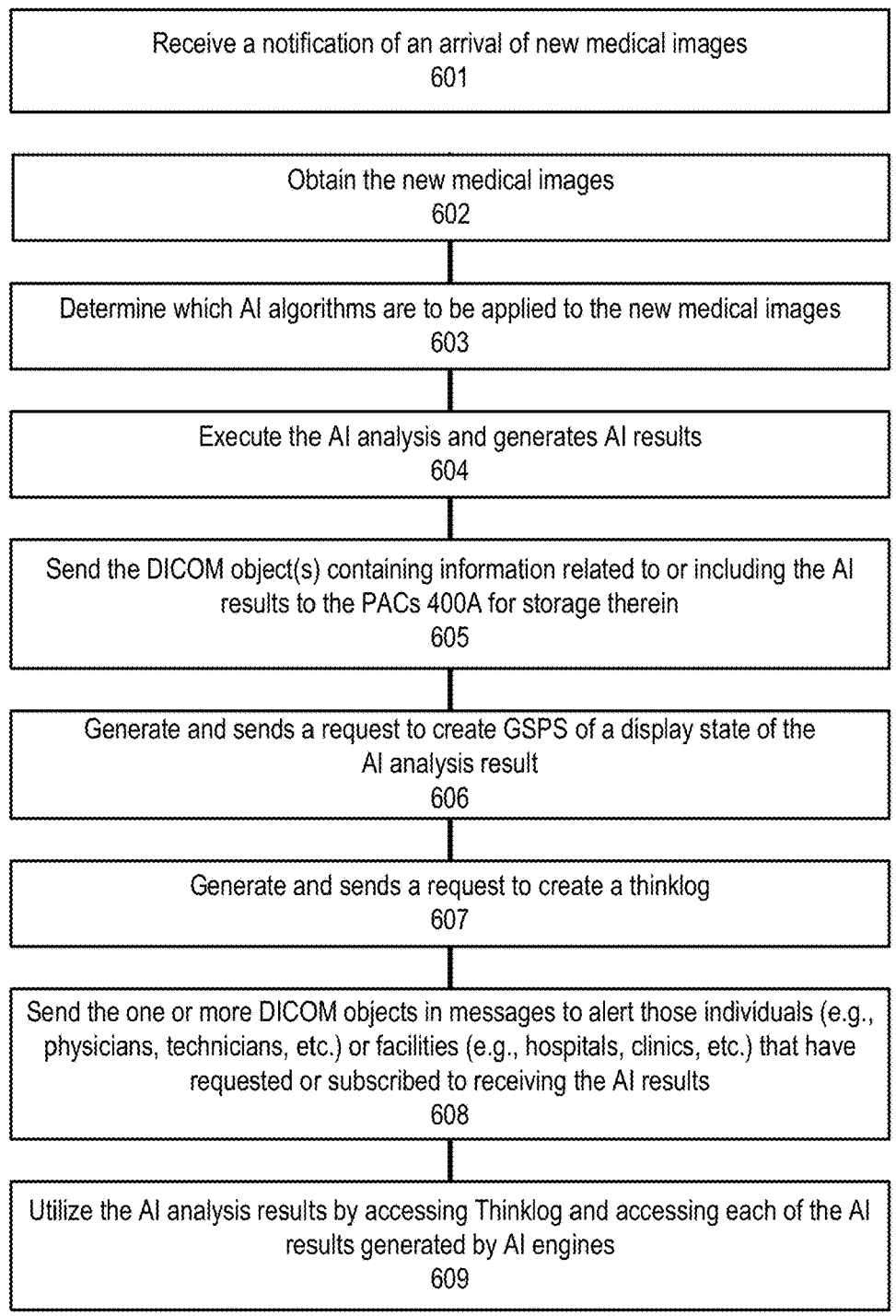
FIG. 6 is a flow diagram of another embodiment of a process for processing medical images using an image analysis (e.g., AI analysis) platform.

FIG. 6 illustrates a more detailed data flow diagram of a process for processing healthcare studies. In one embodiment, the processes are performed by processing logic that may comprise hardware (circuitry, dedicated logic, etc.), software (e.g., software running on a chip), firmware, or a combination of the three. In one embodiment, the process is performed by a medical image management platform, such as, for example, but not limited to, the medical image management platforms described above in conjunction with FIGS. 3, 4A and 4B.

The process begins by applications 401 receiving a notification of an arrival of new medical images (processing block 601). In one embodiment, applications 401 is part of an AI server where one or more AI engines or algorithms are hosted. In another embodiment, the application is an AI engine itself. In one embodiment, the AI algorithm or AI engine is part of a PACS, VNA or other similar medical information management system. The system may have a viewer to display the image analysis results (e.g., AI results).

In one embodiment, the new medical images are part of a new healthcare study. In another embodiment, the new medical images comprise new images added to an existing healthcare study (e.g., a healthcare study that was previously created and already contains medical images (e.g., a series of medical images) and has additional medical images added to it). The images may include DICOM or non-DICOM images.

In one embodiment, applications 401 are notified of the arrival of the new medical images from monitoring and notification logic 402. In one embodiment, monitoring and notification logic 402 continuously monitors the content changes in one or more data sources. The data sources comprise one or more PACS 400A (e.g., DICOM-based PACS, a vendor-specific database, etc.), VNAs 400B (e.g., DICOM-based VNA, a non-DICOM VNA, etc.) or other medical image repositories. The PACS may be a publicly available PACS or a private PACS that is only available to predetermined sets of individuals or institutions (e.g., subscribers). In one embodiment, when a new study arrives or new medical images have been added to an existing study at PACS 400A or VNA 400B, its DICOM server sends a notification to monitoring and notification logic 402.

In one embodiment, study monitoring performed by monitoring and notification logic 402 is achieved either through custom integration or through standard interfaces. For example, as a subscriber, monitoring and notification logic 402 receives a notification using HL7/FHIR standard interfaces indicating that a change in the content at one of the data sources like PACS 400A and VNA 400B. One drawback to using such a standard interface is that the information provided is merely an identification of the study that has been changed without an indication of what change has occurred. Therefore, in response to this notification, the study must be obtained and analyzed to determine the new content that constituted the change before any analyze can be performed. In one embodiment, the notification received by monitoring and notification logic 402 includes information that indicates the specific change in the study. For example, this information may specific the new medical images added to the study. In this case, analysis can start sooner.

In response to receiving notification of new medical images, processing logic obtains the new medical images (processing block 602). In one embodiment, applications 401 obtain the new medical images by obtaining the healthcare study in which they are contained. In one embodiment, applications 401 obtain the healthcare study via DICOM gateway 403 via open API 404.

After obtaining the new medical images, processing logic determines which AI algorithms are to be applied to the new medical images (processing block 603). In one embodiment, information associated with each AI engine when the AI engine was added to the platform indicates its application as far as image analysis is concerned. That is, each AI engine is only applicable for analyzing medical images containing a specific type of medical condition. Thus, when new medical images are obtained, the new medical images are sent only to the AI engines designed for analyzing their specific content. For example, if an AI engine is designed to analyze chest x-rays, only chest x-rays images are sent to the AI engine for analysis.

In one embodiment, the orchestration logic determines the contents of the new medical images in order to identify the proper AI engines to assign to review the images. In one embodiment, the orchestration logic uses information that accompanies the new medical images to determine their contents. In one embodiment the information that accompanies the new medical images is included in header information. For example, in one embodiment, the orchestration logic utilizes various DICOM header-based filters to determine the contents of the new medical images. In another embodiment, the orchestration logic uses built-in body part detection algorithms to decide which AI engine(s) needs to be assigned to evaluate the study. These algorithms analyze the images to determine which body parts are being displayed in the images, and based on this body part detection, the orchestration logic is able to determine the appropriate AI engines to analyze the images. In one embodiment, the orchestration logic only sends a relevant subset of images from the new images to the AI engine. That is, the orchestration logic determines which of the images of the new images have a body part that may be evaluated by a particular AI engine and then only sends those images to the AI engine for analysis. Note that in one embodiment, the orchestration logic determines which AI engines to assign new medical images for analysis using the information that accompanies the new medical images (e.g., header-based information) and the body part detection.

In one embodiment, if the orchestration logic determines that multiple AI engines are to analyze the new medical images (or portions thereof), then the orchestration logic determines a priority among those identified AI engines to control the order in which the AI engines analyze certain images. In one embodiment, the priority is based on the critical nature of that for which the AI engine is analyzing. Thus, if there are two or more AI engines analyzing the new medical images, the orchestration logic assigns a higher priority to the one AI engine evaluating the image for the most critical medical condition and has that AI engine execute first. Note that in one embodiment, if processing power is available, multiple AI engines run at the same time on the same set of images. However, the priority assignment made by the orchestration logic may be across multiple sets of new images from multiple studies that have been received at the same time. In this way, the analysis of the images for more critical medical conditions occurs before analysis for less critical medical conditions. In this way, the techniques described herein better facilitate an early detection system in that the new medical images are analyzed for the most critical conditions before analysis of the less critical conditions.

In one embodiment, the orchestration logic notifies the AI engine to analyze the new medical images. In one embodiment, the orchestration logic notifies the AI engine by sending a notification to the AI engine that includes a study identifier (ID) and a list of one or more images to be analyzed. This is beneficial in that the AI engine is able to focus its analysis on the relevant images from the set of new images instead of having to analyze all of the new images including those that do not contain relevant subject matter to the AI engine. In one embodiment, a list of image or frame identifiers, which could come from multiple studies, is sent although one set is considered the current image or frame and is the target of the AI (as opposed to prior study data). The study ID indicates which is the current study. In general, however, it can be more granular than that (e.g., at the series level, at the image level, at the frame level, etc.).

Once the AI algorithms that are to be applied to the new medical images have been identified and notifications have been sent to the AI engines to analyze the new medical images, processing logic in the AI engines obtains the necessary images to analyze, executes the AI analysis, and generates AI results (processing block 604). In one embodiment, the AI engine obtains the necessary images to analyze by using DICOM gateway 403 and Open API 404.

In one embodiment, processing logic of the AI engines creates findings indicative of the AI results. In one embodiment, the findings comprise one or more DICOM objects containing or that are indicative of at least some aspect of the AI results. In one embodiment, the DICOM objects are created without the AI engine having to be familiar with the DICOM standard. In one embodiment, result object generation module 406 is used by AI engines 405 to create DICOM objects or other outputs containing the findings. The findings may comprise a mask image that is only a relevant portion of one of the new images that shows the finding that is to be reviewed by a physician or clinician. The finding may be a screen shot of the relevant portion of an image that has been captured by the AI engine. In one embodiment, result object generation module 406 captures the portion of the image. The finding may be a heat map related to an image that was analyzed. In one embodiment, the finding may be a snapshot of the raw data. In one embodiment, the DICOM objects that may be generated include DICOM GSPS, DICOM SR, DICOM Basic Structured Display, raw data (DICOM or Non-DICOM), DICOM KOS.

Processing logic sends the DICOM object(s) to the PACS 400A for storage therein (processing block 605). In one embodiment, processing logic sends the DICOM object(s) to the PACS 400A via DICOM gateway 403. In another embodiment, processing logic sends the DICOM object(s) to the VNA 400B. The results may be sent to other locations or destinations as well.

In one embodiment, processing logic optionally generates and sends a request to create GSPS of a display state of the AI analysis result (processing block 606) and/or a thinklog (processing block 607).

In one embodiment, processing logic sends the one or more DICOM objects in messages to alert those individuals (e.g., physicians, technicians, etc.) or facilities (e.g., hospitals, clinics, etc.) that have requested or subscribed to receiving the results (processing block 608). These messages act as notifications and are sent by notification logic. In one embodiment, the notifications are sent to all subscribed applications. This is particularly important in situations where an AI engine has identified a critical medical condition exists or that there is a high likelihood of its existence. In one embodiment, different notification mechanisms are supported by the medical image management system including, for example, but not limited to, WebInvoke, SignalR, HL7 and FHIR in order to allow various types of systems or application can utilize the AI results. Systems consuming the AI result notification include, for example, but not limited to, Radiology Workflow Manager, Image Viewing workstation, Billing IT systems, etc.

In one embodiment, processing logic in applications 401 utilize the AI analysis results by accessing thinklog and then each of the results generated by AI engines (processing block 609). In this case, processing logic retrieves and displays the thinklog, thereby enabling an individual to review the AI result. The thinklog may include a snapshot, such as the snapshot mentioned above. Using the thinklog to review the AI findings is advantageous because the AI findings are stored in the PACS in separate locations and the thinklog places all the AI findings in one place for access in an organized fashion.

While the above process discusses automatically analyzing new medical images occurs in response to notification of the arrival of new images, in one embodiment, individual AI engines can be started manually. In one embodiment, a set of APIs are used to start one of the AI engines. This is needed in cases where the nature of the AI algorithms is such that some preliminary analysis is necessary before the AI engine is engaged. The following are some examples of this. However, it should be noted that other examples are possible.

1. A user wants to analyze a specific part of the image/3d volume by marking an area in image/3d volume using an image viewing application. In this case, the application can invoke APIs to trigger the AI scan by specifying the image points marked by user.

2. A historical study exists and is already stored in VNA or PACS before introducing AI workflow. If user want to perform AI scan on that study, the user can perform it by selecting the study from study list.

3. If user want to perform AI scan through every past study of the patient to determine if a trend exists with respect to a particular abnormality (e.g., a rate of cure), etc., if the facility doesn't configure the system to perform this step automatically because of some reason (e.g., billing concerns, etc.), a user can trigger full scan for the patient by including all his/her prior studies manually.

An Exemplary Medical Imaging Management System

Figure 7:
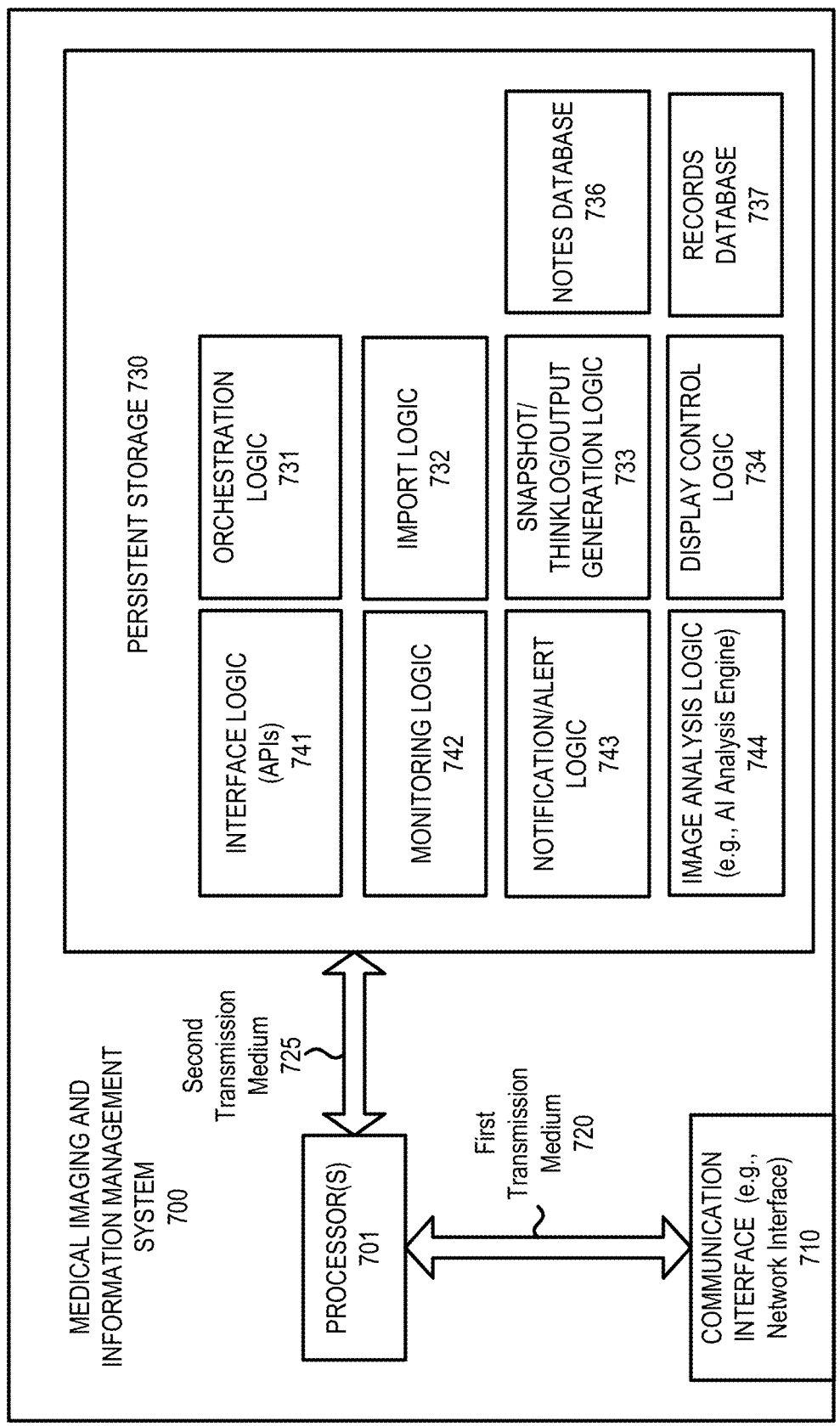
FIG. 7 illustrates an exemplary embodiment of a logical representation of a medical imaging and information management system.

FIG. 7 illustrates an exemplary embodiment of a logical representation of a medical imaging and information management system 700 that generates and renders layouts with current and prior values of parameters discussed above. In one embodiment, system 700 is part of a medical image system such as detailed above.

The medical imaging and information management system 700 includes one or more processors 701 that are coupled to communication interface logic 710 via a first transmission medium 720. The communication interface logic 710 enables communications with other electronic devices, specifically enabling communication with remote users such as doctors, nurses and/or medical technicians, remote databases (e.g., PACS) that store healthcare studies, healthcare modalities that generate and send studies and one or more remote locations (e.g., cloud-based servers) that apply image analysis algorithms (e.g., AI algorithms) to images of studies and generate findings based on the results. According to one embodiment of the disclosure, communication interface logic 710 may be implemented as a physical interface including one or more ports for wired connectors. Additionally, or in the alternative, communication interface logic 710 may be implemented with one or more radio units for supporting wireless communications with other electronic devices.

Processor(s) 701 is further coupled to persistent storage 730 via $2^{nd}$ transmission medium 725. According to one embodiment of the disclosure, persistent storage 730 may include data and code to implement: (a) interface logic 741, (b) monitoring logic 742, (c) notification/alert logic 743, (d) image analysis logic (e.g., AI analysis engine) 744, (e) orchestration logic 731, (f) an import logic 732, (g) a snapshot/thinklog/output generation logic 733, (h) a display control logic 734, (i) a notes database 736 and (j) a records database 737.

In one embodiment, interface logic 741 includes logic for enabling interaction between components in the platform as well as between a user and the display areas being displayed on the display screen. In one embodiment, the interface logic 741 includes the implementations for handling the Open APIs. The user interfaces include the generation of GUIs with studies, or portions thereof, and their associated AI results.

Monitoring logic 742 includes logic for performing continuous monitoring to determine when changes occurred to the data sources, such as PACS systems, VNAs or databases in order to ascertain when new images are available for analysis by AI/image analysis engines.

Orchestration logic 731 includes logic to determine which AI/image analysis engines are to be assigned to analyze new medical images. This logic includes image header and study analysis logic and body part detection logic to identify the contents of medical images, as well as matching logic to compare the results of header/study analysis and body part detection with characteristics of available AI/image analysis algorithms to perform an appropriate assignment. In one embodiment, the orchestration logic 731 is able to receive user input to manually start a scan or review of an existing medical image.

Notification/alert logic 743 includes logic to issue and send notifications to AI/image analysis engines and applications to evaluate one or more new medical images. Notification/alert logic 743 also generates and send notifications and/or alerts for reviews of studies, including AI/image analysis results, to one or more of physicians and medical personnel. In one embodiment, notification/alert logic 743 sends an alert (e.g., SMS, text, email, or other message, a chat indication indicating a chat session is desired with the physician, etc.) in response to a predetermined finding in the results of automated image analysis performed one or more image of a healthcare study. In one embodiment, the predetermined finding comprises an abnormality score above a threshold level. In another embodiment, the predetermined finding comprises one or more keywords in the findings. In yet another embodiment, the predetermined finding comprises an abnormality score above a threshold level and one or more keywords in the findings. In one embodiment, the alert is sent to one or more predetermined healthcare providers responsible for handling a condition associated with the predetermined finding. For example, in one embodiment, if the findings indicate the patient has likely experienced a brain stroke, an alert is automatically sent to a stroke team at a particular medical facility to take care of the patient. In one embodiment, the alert includes a link to an image related to the findings of the health care study that were generated by the automated image analysis algorithm. In such a case, the alert may include a link that the user selects to open a study containing the image associated with finding and the system displays the image.

Image analysis logic 744 performs one or more image analysis algorithms on images from healthcare studies. In one embodiment, the image analysis algorithms are AI analysis algorithms. The results from applying the image analysis algorithms may be displayed on a screen.

Import logic 732 may include logic for retrieving one or more pieces of information from a storage device and importing each of the one or more pieces of information into a separate display area of a viewer or viewer template. For example, the pieces of information may include, but are not limited or restricted to, (i) findings from automated image analysis algorithms (e.g., AI algorithms); (ii) medical images, including x-rays, mammograms, computerized tomography (CT) scans, magnetic resonance imaging (MRI), positron emission tomography (PET) scan and/or ultrasound imaging, (iii) physician's notes regarding one or more of the medical images and/or (iv) medical records corresponding to one or more of the subjects of the one or more medical images.

Snapshot/thinklog/output generation logic 733 includes logic for generating a snapshot (by saving the state of the layout template) a thinklog and/or an AI/image analysis output as described above. Saving the state may include storing, at least, (i) the one or more pieces of information, and (ii) viewing properties of each of the one or more pieces of information in a non-transitory computer-readable medium. The layout template may depict one or more images of a healthcare study that depicts image data that is relevant to a finding from an automated image analysis algorithm. Snapshot/thinklog/output generation logic 733 is able to save the snapshot, thinklog or AI/image analysis result into a medical record or report and/or send it to a predetermined location.

Display control logic 734 includes logic for displaying user interfaces, images, and AI/image analysis results that have been rendered locally as discussed above. In one embodiment, display control logic 734 includes logic to display a browser into which the images, user interfaces described above, are displayed.

Notes database 736 stores notes recorded by a doctor, nurse, medical technician, etc., that a user may import into a display area of a layout template. Finally, records database 737 stores medical records that a user may import into a display area of a layout template.

There is a number of example embodiments described herein.

Example 1 is a method comprising: monitoring, by a medical image management system, for a first indication of a content change at one or more data sources; determining, in response to the first indication, which of a plurality of image analysis engines is to analyze at least one image of one or more new medical images associated with the content change based on one or both of information accompanying the one or more images or results of applying body part detection on the at least one image; sending a first notification to start image analysis on the at least one image of the one or more medical images, the first notification being sent to each image analysis engine in a set of one or more image analysis engines determined to analyze the at least one image of the one or more new medical images; receiving a second indication that image analysis results are available from the set of one or more image analysis engines; and sending a second notification to subscribers to indicate availability of image analysis results for access and display thereby.

Example 2 is the method of example 1 that may optionally include that one or more image analysis engines of the plurality of image analysis engines comprises an artificial intelligence (AI) engine.

Example 3 is the method of example 1 that may optionally include that the first indication specifies arrival of the one or more new medical images to the one or more data sources.

Example 4 is the method of example 1 that may optionally include that the one or more new medical images are part of a new health care study or an existing study created prior to generation of the new medical images.

Example 5 is the method of example 1 that may optionally include determining a priority for each image analysis engine determined to analyze the at least one image when multiple image analysis engines.

Example 6 is the method of example 5 that may optionally include that determining the priority is based on features in a healthcare study of the at least one image, priors, and a nature of the multiple image analysis engines.

Example 7 is the method of example 1 that may optionally include, in response to receiving the notification, determining, using the image analysis engine, whether one or more features in the at least one image meet predefined criteria indicative of a medical condition; generating, by the image analysis engine, a DICOM compliant AI result representation without implementing DICOM conformance; and sending the DICOM compliant AI result representation as a DICOM object to the medical image management system.

Example 8 is the method of example 7 that may optionally include that the one or more features include one or more of anatomical features and abnormalities set forth in the medical image.

Example 9 is the method of example 7 that may optionally include that the image analysis engine is operable to perform image analysis to determine whether the one or more features in the at least one image meet the predefined criteria without user input.

Example 10 is a medical image management system comprising: a network communication interface to receive healthcare studies; a memory coupled to the network communication interface to store received healthcare studies; a display screen coupled to the memory to display the received healthcare studies; and one or more processors coupled to the network connection interface, the memory and the display screen and configured to monitor for a first indication of a content change at one or more data sources; determine, in response to the first indication, which of a plurality of image analysis engines is to analyze at least one image of one or more new medical images associated with the content change based on one or both of information accompanying the one or more images or results of applying body part detection on the at least one image; send a first notification to start image analysis on the at least one image of the one or more medical images, the first notification being sent to each image analysis engine in a set of one or more image analysis engines determined to analyze the at least one image of the one or more new medical images; receive a second indication that image analysis results are available from the set of one or more image analysis engines; and send a second notification to subscribers to indicate availability of image analysis results for access and display thereby.

Example 11 is the system of example 10 that may optionally include that one or more image analysis engines of the plurality of image analysis engines comprises an artificial intelligence (AI) engine.

Example 12 is the system of example 10 that may optionally include that the first indication specifies arrival of the one or more new medical images to the one or more data sources.

Example 13 is the system of example 12 that may optionally include that the one or more new medical images are part of a new health care study or an existing study created prior to generation of the new medical images.

Example 14 is the system of example 10 that may optionally include that the one or more processors is operable to determine a priority for each image analysis engine determined to analyze the at least one image when multiple image analysis engines.

Example 15 is the system of example 14 that may optionally include that determining the priority is based on features in a healthcare study of the at least one image, priors, and a nature of the multiple image analysis engines.

Example 16 is a non-transitory computer readable storage media having instructions stored thereupon which, when executed by a system having at least a processor, a memory and a display screen therein, cause the system to perform a method comprising: monitoring for a first indication of a content change at one or more data sources; determining, in response to the first indication, which of a plurality of image analysis engines is to analyze at least one image of one or more new medical images associated with the content change based on one or both of information accompanying the one or more images or results of applying body part detection on the at least one image; sending a first notification to start image analysis on the at least one image of the one or more medical images, the first notification being sent to each image analysis engine in a set of one or more image analysis engines determined to analyze the at least one image of the one or more new medical images; receiving a second indication that image analysis results are available from the set of one or more image analysis engines; and sending a second notification to subscribers to indicate availability of image analysis results for access and display thereby.

Example 17 is the computer readable storage media of example 16 that may optionally include that one or more of image analysis engines of the plurality of image analysis engines comprises an artificial intelligence (AI) engine.

Example 18 is the computer readable storage media of example 16 that may optionally include that the first indication specifies arrival of the one or more new medical images to the one or more data sources.

Example 19 is the computer readable storage media of example 18 that may optionally include that the one or more new medical images are part of a new health care study or an existing study created prior to generation of the new medical images.

Example 20 is the computer readable storage media of example 16 that may optionally include that the method further comprises determining a priority for each image analysis engine determined to analyze the at least one image when multiple image analysis engines.

Example 21 is the computer readable storage media of example 20 that may optionally include that determining the priority is based on features in a healthcare study of the at least one image, priors, and a nature of the multiple image analysis engines.

Example 22 is the computer readable storage media of example 16 that may optionally include that the method further comprises, in response to receiving the notification, determining, using the image analysis engine, whether one or more features in the at least one image meet predefined criteria indicative of a medical condition; generating, by the image analysis engine, a DICOM compliant AI result representation without implementing DICOM conformance; and sending the DICOM compliant AI result representation as a DICOM object to the medical image management system.

Example 23 is the computer readable storage media of example 22 that may optionally include that the one or more features include one or more of anatomical features and abnormalities set forth in the medical image.

Example 24 is the computer readable storage media of example 22 that may optionally include that the image analysis engine is operable to perform image analysis to determine whether the one or more features in the at least one image meet the predefined criteria without user input.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

We claim:

1. A method comprising:
    monitoring, by a medical image management system, for a first indication of a content change at one or more data sources;
    obtaining one or more new medical images associated with the content change in response to the first indication;
    determining which of a plurality of image analysis engines is to analyze at least one image of the one or more new medical images based on at least one item selected from the group consisting of: information accompanying the one or more new medical images and results of applying body part detection on the at least one image, wherein analyzing the at least one image based on the information accompanying the one or more new medical images and the results of applying body part detection on the at least one image determines the contents of the at least one image of the one or more new medical images;
    sending a first notification to start image analysis on the at least one image of the one or more new medical images, the first notification being sent to each image analysis engine in a set of one or more image analysis engines determined to analyze the at least one image of the one or more new medical images;
    receiving a second indication that image analysis results are available from the set of one or more image analysis engines; and
    sending a second notification to subscribers to indicate availability of image analysis results for access and display thereby.

2. The method defined in claim 1, wherein one or more of the plurality of image analysis engines comprises an artificial intelligence (AI) engine.

3. The method defined in claim 1, wherein the first indication specifies arrival of the one or more new medical images to the one or more data sources.

4. The method defined in claim 3, wherein the one or more new medical images are part of a new health care study or an existing study created prior to generation of the new medical images.

5. The method defined in claim 1, further comprising: determining a priority for each image analysis engine determined to analyze the at least one image when multiple image analysis engines.

6. The method defined in claim 5, wherein determining the priority is based on features in a healthcare study of the at least one image, priors, and a nature of the multiple image analysis engines.

7. The method defined in claim 1, further comprising, in response to receiving the notification:
   determining, using the image analysis engine, whether one or more features in the at least one image meet predefined criteria indicative of a medical condition;
   generating, by the image analysis engine, a Digital Imaging and Communications in Medicine (DICOM) compliant AI result representation without implementing DICOM conformance; and
   sending the DICOM compliant AI result representation as a DICOM object to the medical image management system.

8. The method defined in claim 7, wherein the one or more features include one or more of anatomical features and abnormalities set forth in the medical image.

9. The method defined in claim 7, wherein the image analysis engine is operable to perform image analysis to determine whether the one or more features in the at least one image meet the predefined criteria without user input.

10. The method of claim 1, wherein the determining is based on information accompanying the one or more new medical images, and wherein the information comprises header information.

11. A medical image management system comprising:
   a network communication interface to receive healthcare studies;
   a memory coupled to the network communication interface to store received healthcare studies;
   a display screen coupled to the memory to display the received healthcare studies; and
   one or more processors coupled to the network connection interface, the memory and the display screen and configured to:
      monitor for a first indication of a content change at one or more data sources;
      obtain one or more new medical images associated with the content change in response to the first indication;
      determine which of a plurality of image analysis engines is to analyze at least one image of the one or more new medical images based on at least one item selected from the group consisting of: information accompanying the one or more new medical images and results of applying body part detection on the at least one image, wherein analyzing the at least one image based on the information accompanying the one or more new medical images and the results of applying body part detection on the at least one image determines the contents of the at least one image of the one or more new medical images;
      send a first notification to start image analysis on the at least one image of the one or more new medical images, the first notification being sent to each image analysis engine in a set of one or more image analysis engines determined to analyze the at least one image of the one or more new medical images;
      receive a second indication that image analysis results are available from the set of one or more image analysis engines; and
      send a second notification to subscribers to indicate availability of image analysis results for access and display thereby.

12. The system defined in claim 11, wherein one or more of the plurality of image analysis engines comprises an artificial intelligence (AI) engine.

13. The system defined in claim 11, wherein the first indication specifies arrival of the one or more new medical images to the one or more data sources.

14. The system defined in claim 13, wherein the one or more new medical images are part of a new health care study or an existing study created prior to generation of the new medical images.

15. The system defined in claim 11, wherein the one or more processors is operable to determine a priority for each image analysis engine determined to analyze the at least one image when multiple image analysis engines.

16. The system defined in claim 15, wherein determining the priority is based on features in a healthcare study of the at least one image, priors, and a nature of the multiple image analysis engines.

17. A non-transitory computer readable storage media having instructions stored thereupon which, when executed by a system having at least a processor, a memory and a display screen therein, cause the system to perform a method comprising:
   monitoring for a first indication of a content change at one or more data sources;
   determining, in response to the first indication, which of a plurality of image analysis engines is to analyze at least one image of one or more new medical images associated with the content change based on at least one item selected from the group consisting of: information accompanying the one or more new medical images and results of applying body part detection on the at least one image, wherein analyzing the at least one image based on the information accompanying the one or more new medical images and the results of applying body part detection on the at least one image determines the contents of the at least one image of the one or more new medical images;
   sending a first notification to start image analysis on the at least one image of the one or more new medical images, the first notification being sent to each image analysis engine in a set of one or more image analysis engines determined to analyze the at least one image of the one or more new medical images;
   receiving a second indication that image analysis results are available from the set of one or more image analysis engines; and
   sending a second notification to subscribers to indicate availability of image analysis results for access and display thereby.

18. The computer readable storage media defined in claim 17, wherein one or more of the plurality of image analysis engines comprises an artificial intelligence (AI) engine.

19. The computer readable storage media defined in claim 17, wherein the first indication specifies arrival of the one or more new medical images to the one or more data sources.

20. The computer readable storage media defined in claim 19, wherein the one or more new medical images are part of a new health care study or an existing study created prior to generation of the new medical images.

21. The computer readable storage media defined in claim 17, further comprising: determining a priority for each image analysis engine determined to analyze the at least one image when multiple image analysis engines.

22. The computer readable storage media defined in claim 17, further comprising, in response to receiving the notification:
- determining, using the image analysis engine, whether one or more features in the at least one image meet predefined criteria indicative of a medical condition;
- generating, by the image analysis engine, a Digital Imaging and Communications in Medicine (DICOM) compliant AI result representation without implementing DICOM conformance; and
- sending the DICOM compliant AI result representation as a DICOM object to the medical image management system.

23. The computer readable storage media defined in claim 22, wherein the one or more features include one or more of anatomical features and abnormalities set forth in the medical image.

24. The computer readable storage media defined in claim 22, wherein the image analysis engine is operable to perform image analysis to determine whether the one or more features in the at least one image meet the predefined criteria without user input.

* * * * *